United States Patent [19]

Daines

[11] Patent Number: 5,643,914
[45] Date of Patent: Jul. 1, 1997

[54] PHARMACEUTICAL PYRIDINE COMPOUNDS

[75] Inventor: Robert A. Daines, Lansdale, Pa.

[73] Assignee: SmithKline Beecham Corporation, Philadelphia, Pa.

[21] Appl. No.: 356,358

[22] PCT Filed: Jun. 30, 1993

[86] PCT No.: PCT/US93/06234

§ 371 Date: Dec. 19, 1994

§ 102(e) Date: Dec. 19, 1994

[87] PCT Pub. No.: WO94/00437

PCT Pub. Date: Jan. 6, 1994

[51] Int. Cl.$^6$ .................. A61K 31/435; A61K 31/44; C07D 401/00; C07D 211/72
[52] U.S. Cl. .................. 514/277; 514/284; 514/336; 514/340; 514/342; 514/348; 514/350; 514/354; 514/381; 546/269.7; 546/280.4; 546/290; 546/296; 546/298; 546/299; 546/300; 546/301; 546/323; 546/329; 546/330; 546/334; 546/335; 546/336; 546/337; 546/339; 546/340; 546/341; 546/344; 546/346
[58] Field of Search .................. 546/275, 284, 546/290, 296, 298, 299, 300, 301, 302, 303, 323, 329, 330, 334, 335, 336, 337, 339, 340, 341, 342, 344, 346; 514/277, 336, 340, 342, 348, 350, 351, 354, 381

[56] References Cited

U.S. PATENT DOCUMENTS

| | | | |
|---|---|---|---|
| 4,056,619 | 11/1977 | Connor et al. | 424/263 |
| 4,438,271 | 3/1984 | Bell et al. | 71/94 |
| 4,508,562 | 4/1985 | Nakayama et al. | 546/294 |
| 4,794,188 | 12/1988 | Musser et al. | 546/152 |

FOREIGN PATENT DOCUMENTS

| | | |
|---|---|---|
| 0 318 083 | 3/1989 | European Pat. Off. . |
| WO91/18601 | 12/1991 | WIPO . |

OTHER PUBLICATIONS

Chem. Abstracts 110:231630m, Szczepanski et al., 19 Jun. 1989.

Chem. Abstracts 25 Feb. 1959; Plieninger, H., et al.; (Chem. Ber. 91, 1989).

Chemical Abstract: 83: 163953r 1975 (Reimann et al.) (pp. 528–529).

*Primary Examiner*—Shean C. Wu
*Attorney, Agent, or Firm*—James M. Kanagy; Stephen Venetianer; Edward T. Lentz

[57] ABSTRACT

This invention relates to a compound of formula 1

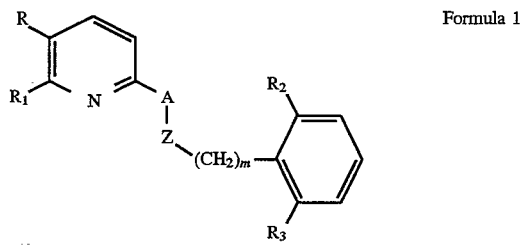

Formula 1 or an N-oxide, or a pharmaceutically acceptable salt, where

A is $CH_2$ and Z is $S(O)_q$ where q is 0, 1 or 2, $CH_2$, CHOH, CO, $NR_x$, or O, or A is C=O and Z is $NR_x$;

m is 0–5;

$R_x$ is hydrogen or lower alkyl;

R is $C_1$ to $C_{20}$-aliphatic, unsubstituted or substituted five-membered heteroaryl-$C_1$ to $C_{10}$-aliphatic-O—, unsubstituted or substituted phenyl-$C_1$ to $C_{10}$-aliphatic where substituted p from the group consisting of lower alkoxy, lower alkyl, trihalomethyl, and halo, or R is $C_1$ to $C_{20}$-aliphatic-O—, or R is unsubstituted or substituted phenyl-$C_1$ to $C_{10}$-aliphatic-O— where substituted phenyl has one or more radicals selected from the group consisting of lower alkoxy, lower alkyl, trihalomethyl, and halo;

$R_1$ is $R_4$, —($C_1$ to $C_5$ aliphatic)$R_4$, —($C_1$ to $C_5$ aliphatic)CHO, —($C_1$ to $C_5$ aliphatic)$CH_2OR_5$;

$R_2$ and $R_3$ are independently, halo, lower alkoxy, $CF_3$, CN, or lower alkyl;

$R_4$ is tetrazol-5-yl or COOH or an ester or amide thereof; and $R_5$ is H, lower alkyl, $CH_3(CH_2)_{0-6}CO$ or phenyl$(CH_2)_{0-3}CO$.

This compound is leukotriene antagonist and can be used in treating various diseases associated with leukotrienes.

14 Claims, No Drawings

PHARMACEUTICAL PYRIDINE COMPOUNDS

SCOPE OF THE INVENTION

This application a 371 of PCT/U.S. 93/06234 filed Jun. 3, 1993.

The field of this invention is that of certain substituted pyridinyl-2-propenoates, and homologs thereof, which have been found to be useful for treating diseases arising from or related to leukotrienes, particularly leukotriene $B_4$. As such there utility lies in antagonizing the affects of leukotrienes.

BACKGROUND OF THE INVENTION

The family of bioactive lipids known as the leukotrienes exert pharmacological effects on respiratory, cardiovascular and gastrointestinal systems. The leukotrienes are generally divided into two sub-classes, the peptidoleukotrienes leukotrienes $C_4$, $D_4$ and $E_4$) and the dihydroxyleukotrienes (leukotriene $B_4$). This invention is primarily concerned with the hydroxyleukotrienes (LTB) but is not limited to this specific group of leukotrienes.

The peptidoleukotrienes are implicated in the biological response associated with the "Slow Reacting Substance of Anaphylaxis" (SRS-A). This response is expressed in vivo as prolonged bronchoconstriction, in cardiovascular effects such as coronary artery vasoconstriction and nnmerous other biological responses. The pharmacology of the peptidoleukotrienes include smooth muscle contractions, myocardial depression, increased vascular permeability and increased mucous production.

By comparison, $LTB_4$ exerts its biological effects through stimulation of leukocyte and lymphocyte functions. It stimulates chemotaxis, chemokinesis and aggregation of polymorphonuclear leukocytes (PMNs).

Leukotrienes are critically involved in mediating many types of cardiovascular, pulmonary, dermatological, renal, allergic, and inflammatory diseases including asthma, adult respiratory distress syndrome, cystic fibrosis, psoriasis, and inflammatory bowel disease.

Leukotriene $B_4$ ($LTB_4$) was first described by Borgeat and Samuelsson in 1979, and later shown by Corey and co-workers to be 5(S),12(R)-dihydroxy-(Z,E,E,Z)-6,8,10, 14-eicosatetraenoic acid.

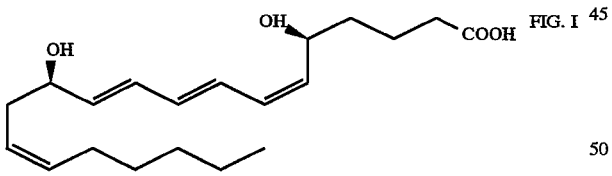

FIG. 1

It is a product of the arachidonic add cascade that results from the enzymatic hydrolysis of $LTA_4$. It has been found to be produced by mast cells, polymorphononuclear leukocytes, monocytes and macrophages. $LTB_4$ has been shown to be a potent stimulus in vivo for PMN leukocytes, causing increased chemotactic and chemokinetic migration, adherence, aggregation, degranulation, superoxide production and cytotoxicity. The effects of $LTB_4$ are mediated through distinct receptor sites on the leukocyte cell surface that exhibit a high degree of stereospecificity. Pharmacological studies on human blood PMN leukocytes indicate the presence of two classes of $LTB_4$-specific receptors that are separate from receptors specific for the peptide chemotactic factors. Each of the sets of receptors appear to be coupled to a separate set of PMN leukocyte functions. Calcium mobilization is involved in both mechanisms.

$LTB_4$ has been established as an inflammatory mediator in vivo. It has also been associated with airway hyper-responsiveness in the dog as well as being found in increased levels in lung lavages from humans with severe pulmonary dysfunction.

By antagonizing the effects of $LTB_4$, or other pharmacologically active mediators at the end organ, for example airway smooth muscle, the compounds and pharmaceutical compositions of this invention are valuable in the treatment of diseases in subjects, including human or animals, in which leukotrienes are a factor.

SUMMARY OF THE INVENTION

In a first aspect, this invention covers a compound of formula I

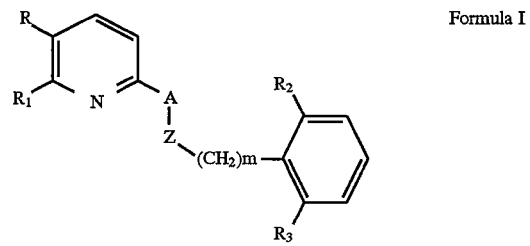

Formula I or an N-oxide, or a pharmaceutically acceptable salt, where

A is $CH_2$ and Z is $S(O)q$ where q is 0, 1 or 2, $CH_2$, CHOH, C=O, or $NR_x$, or O; or A is C=O and Z is $NR_x$;

m is 0–5;

$R_x$ is hydrogen or lower alkyl;

R is $C_1$ to $C_{20}$-aliphatic, unsubstituted or substituted five-membered heteroaryl-$C_1$ to $C_{10}$-aliphatic-O—, unsubstituted or substituted phenyl—$C_1$ to $C_{10}$-aliphatic where substituted phenyl has one or more radicals selected from the group consisting of lower alkoxy, lower alkyl, trihalomethyl, and halo, or R is $C_1$ to $C_{20}$-aliphatic-O—, or R is unsubstituted or substituted phenyl-$C_1$ to $C_{10}$-aliphatic-O— where substituted phenyl has one or more radicals selected from the group consisting of lower alkoxy, lower alkyl, trihalomethyl, and halo;

$R_1$ is $R_4$, —($C_1$ to $C_5$ aliphatic)$R_4$, —($C_1$ to $C_5$ aliphatic) CHO, —($C_1$ to $C_5$ aliphatic)$CH_2OR_5$;

$R_2$ and $R_3$ are independently, halo, lower alkoxy, $CF_3$, CN, or lower alkyl;

$R_4$ is tetrazol-5-yl or COOH or an ester or amide thereof; and $R_5$ is H, lower alkyl, $CH_3(CH_2)_{0-6}CO$ or phenyl $(CH_2)_{0-3}CO$.

In a further aspect, this invention relates to compositions comprising a compound of formula I, or a salt thereof, in admixture with a carrier. Included in these compositions are those suitable for pharmaceutical use and comprising a pharmaceutically acceptable excipient or carrier and a compound of formula I which may be in the form of a pharmaceutically acceptable salt.

These compounds can also be used for treating diseases, particularly psoriasis and inflammatory bowel disease.

Processes for making these compounds are also included in the scope of this invention, which processes comprise:

a) forming a salt, or b) forming an ester;

c) oxidizing a thio ether to the sulfoxide or sulfone; or d) forming a compound of formula I by treating a 6-halomethylpyridyl compound with the appropriate mercaptan, hydroxy, or amino compound.

GENERAL EMBODIMENTS

The following definitions are used in describing this invention.

"Aliphatic" is intended to include saturated and unsaturated radicals. This includes normal and branched chains, saturated or mono or poly unsaturated chains where both double and triple bonds may be present in any combination. The phrase "lower alkyl" means an alkyl group of 1 to 6 carbon atoms in any isomeric form, but particularly the normal or linear form. "Lower alkoxy" means the group lower alkyl—O—. "Acyl-lower alkyl" refers to the group (O)C-lower alkyl where the carbonyl carbon is counted as one of the carbons of the 1 to 6 carbons noted under the definition of lower alkyl. "Halo" refers to and means fluoro, chloro, bromo or iodo. The phenyl ring may be substituted with one or more of these radicals. Multiple substituents may be the same or different, such as where there are three chloro groups, or a combination of chloro and alkyl groups and further where this latter combination may have different alkyl radicals in the chloro/alkyl pattern.

The phrase "unsubstituted or substituted five-membered heteroaryl" means a five-membered aromatic ring which has one or more hetero atoms which are oxygen, sulfur or nitrogen. Examples of such rings are furyl, thienyl, tetrazolyl, thiazolyl, isothiazolyl, triazolyl, oxazolyl, isoxazolyl, thiadiazolyl, pyrrolyl, imidazolyl or pyrazolyl. Rings may be substituted with one or more lower alkyl groups, preferably methyl.

The phrase "a pharmaceutically acceptable ester-forming group" covers all esters which can be made from the acid function(s) which may be present in these compounds. The resultant esters will be ones which are acceptable in their application to a pharmaceutical use. By that it is meant that the esters will retain the biological activity of the parent compound and will not have an untoward or deleterious effect in their application and use in treating diseases.

Amides may be formed from acid groups. The most preferred amides are those where the nitrogen is substituted by hydrogen or alkyl of 1 to 6 carbons. The diethylamide is particularly preferred.

Pharmaceutically acceptable salts of the instant compounds are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. The parent compound, dissolved in a suitable solvent, is treated with an excess of an organic or inorganic acid, in the case of acid addition salts of a base, or an excess of organic or inorganic base where $R_4$ is COOH for example.

Oxides of the pyridyl ring nitrogen may be prepared by means known in the art and as illustrated herein. These are to be considered part of the invention.

If by some combination of substituents, a chiral center is created or another form of an isomeric center is created in a compound of this invention, all formula of such isomer(s) are intended to be covered herein. Compounds with a chiral center may be administered as a racemic mixture or the racemates may be separated and the individual enantiomer used alone.

As leukotriene antagonists, these compounds can be used in treating a variety of diseases associated with or attributing their origin or affect to leukotrienes, particularly $LTB_4$. Inflammatory diseases such as psoriasis and inflammatory bowel disease may be treated by applying or administering the compounds described herein. It is also expected that these compounds can be used to treat allergic diseases including those of a pulmonary and non-pulmonary nature. For example these compounds will be useful in antigen-induced anaphylaxis. They are useful in treating asthma, allergic rhinitis and irritable bowel disease. Ocular diseases such as uveitis, and allergic conjunctivitis can also be treated by these compounds.

Preferred compounds are those where R is $C_8$ to $C_{20}$ alkoxy, thienyl-$C_1$ to $C_{10}$ alkoxy, unsubstituted or substituted thiazolyl-$C_1$ to $C_{10}$ alkoxy, phenyl-$C_1$ to $C_{10}$ alkoxy or substituted-phenyl$C_1$ to $C_{10}$ alkoxy; $R_1$ is —($C_1$–$C_3$alkyl)$R_4$, or —($C_2$–$C_3$alkenyl)$R_4$ and $R_2$ and $R_3$, are both halo. The more preferred compounds are those where R is substituted phenyl-$C_1$ to $C_{10}$ alkoxy, particularly the unsubstituted-phenyl($CH_2$)$_{2-8}$-O—group, or the p-fluoro or p-methoxyphenyl($CH_2$)$_{2-8}$-O—group, or $CH_3(CH_2)_{7-9}$-O—; m is 0–5, most preferably 0, 1, or 2; $R_1$ is $HO_2C$—CH=CH—, or $HO_2C$—$CH_2CH_2$— or a salt, ester or amide derivative thereof. As regards A, the $CH_2$ group is preferred. As regards Z, $S(O)_q$ and O are preferred. Another sub-group of preferred compounds are those where $R_2$ and $R_3$ are halo methyl or methoxy, particularly where both are halo, methyl or methoxy. The 2,6-dichloro dichloro is a preferred compound. Specific preferred compounds are:

(E)-sodium 3-[3-[4-(4-methoxyphenyl)butyloxy]-6-[(2,6-fluorophenylthio)methyl]-2-pyridinyl]-2-propenoate, (E)-sodium 3-[3-[4-(4-methoxyphenyl)butyloxy]-6-[(2,6-dimethylphenylthio)methyl]-2-pyridinyl]-2-propenoate, (E)-sodium 3-[3-[4-(4-methoxyphenyl)butyloxy]-6-[(2,6-dimethoxyphenylthio)methyl]-2-pyridinyl]-2propenoate, (E)-lithium 3-[3-[4-(4-methoxyphenyl)butyloxy]-6-[(2,6-dichlorophenylthio)methyl]-2-pyridinyl]-2-propenoate, (E)-sodium 3-[3-[4-(4-fluorophenyl)butyloxy]-6-[(2,6-dichlorophenylthio)methyl]-2-pyridinyl]-2-propenoate, (E)-sodium3-[3-[4-(4-fluorophenyl)butyloxy]-6-[(2,6-difluorophenylthio)methyl]-2-pyridinyl]-2-propenoate, (E)-sodium 3-[3-[2-(4-fluorophenyl)ethyloxy]-6-[(2,6-dichlorophenylthio)methyl]-2-pyridinyl]-2-propenoate, (E)-sodium 3-[3-[2-(4-fluorophenyl)ethyloxy]-6-[(2,6-difluorophenylthio)methyl]-2-pyridinyl]-2-propenoate, (E)-sodium 3-[3-(4-fluorobenzyloxy)-6-[(2,6-dichlorophenylthio)methyl]-2-pyridinyl]-2-propenoate, (E)-sodium 3-[3-[4-phenylbutyloxy]-6-[(2,6-dichlorophenylthio)methyl]-2-pyridinyl]-2-propenoate, (E)-sodium 3-[3-[4-phenylethyloxy]-6-[(2,6-dichlorophenylthio)methyl]-2-pyridinyl]-2-propenoate, (E)-sodium 3-[3-[2-(4-fluorophenyl)ethyloxy]-6-[(2,6-dichlorophenylthio)methyl]-2-pyridinyl]-2-propanoate, (E)-sodium 3-[3-[4-(4-fluorophenyl)butyloxy]-6-[2,6-dichlorophenylthio)methyl]-2-pyridinyl]-2-propanoate, (E)-sodium 3-[3-[4-(4-methoxyphenyl)butyloxy]-6-[(2,6-dichlorophenylthio)methyl]-2-pyridindyl]-2-propenoate, (E)-sodium 3-[3-[2-(4-methoxyphenyl)ethyloxy]-6[(2,6-dichlorophenylthio)methyl]-2-pyridinyl]-2-propenoate, (E)-sodium 3-[3-[2-(4-fluorophenyl)ethyloxy]-6[(2,4,6-trichlorophenylthio)methyl]-2-pyridinyl]-2-propenoate, (E)-sodium 3-[3-[2-(4-fluorophenyl)ethyloxy]-6[(2-chloro-6-methylphenylthio)methyl]-2-pyridinyl]-2-propenoate, (E)-sodium 3-[3-[2-(4-methoxyphenyl)ethyloxy]-6[(2,6-dichlorophenylthio)methyl]-2-pyridinyl]-2-propanoate, (E)-3-[3-[2-(4-chlorophenyl)ethyloxy]-6[(2,6-dichlorophenylthio)methyl]-2-pyridinyl]-2-propenoic acid, (E)-3-[3-[8-(4-methoxyphenyl)octyloxy]-6-[(2,6-dichlorophenylthio)methyl]-2-pyridinyl]-2-propenoic acid, (E)-3-[3-[2-phenethyloxy]-6-[(2,6-dichlorophenylthio)methyl]-2-pyridinyl]-2-propenoic acid, (E)-3-[3-[3-phenylpropyloxy]-6-[(2,6-dichlorophenylthio)methyl]-2-pyridinyl]-2-propenoic acid, (E)-N,N-diethyl 3-[3-[2-phenethyloxy]-6[(2,6-dichlorophenylthio)methyl]-2-pyridinyl]-2-propenamide, (E)-3-[3-[2-phenethyloxy]-6-[(2,6-dichlorophenyloxy)methyl]-2-pyridinyl]-2-propenoic acid, (E)-3-[3-[2-(thien-2-yl)ethyloxy]-6-[(2,6-dichlorophenylthio)methyl]-2-pyridinyl]-2-propenoic acid, (E)-3-[3-[2-(thien-3-yl)ethyloxy]-6-[(2,6-dichlorophenylthio)methyl]-2-pyridinyl]-2-propenoic acid, (E)-3-[3-[2-(3-methylthiazol-2-yl)ethyloxy]-6[(2,6-dichlorophenylthio)methyl]-2-pyridinyl]-2-propenoic acid, (E)-N,N-diethyl 3-[3-[2-phenethyloxy]-6[(2,6-dichlorophenylthio)methyl]-2-pyridinyl]-2-propenamide, or a free acid thereof or another pharmaceutically acceptable salt.

SYNTHESIS

Several methods, variations on the same process, have been used for preparing these compounds. In general, the approach taken was to first make the intermediates needed to make the R group, then to prepare the phenyl intermediate needed for forming the core structure of formula I; the pyridyl intermediate was then prepared and reacted with the phenyl intermediate to form the core structure. Salts, free acids, amides, alternative esters and the like were then prepared.

As noted, the first step was to make the intermediates needed for forming those R groups where the intermediates were not available commercially. This chemistry is illustrated for the case of the substituted phenyl-$C_1$ to $C_{10}$-aliphatic-O— groups. The same or similar chemistry has been disclosed in published patent applications, for example PCT international application numbers PCT/US 91/03398, PCT/US 91/03772, PCT/US 91/03940, and PCT/US 91/03399. All are reference. The chemistries set out in those documents can be used in place of or in conjunction with those given here to prepare the R groups of formula I.

Usually the substituted pyridylchloride is prepared next, as opposed to the thiol intermediate, but this is not critical to the practice of the invention. Making the substituted 6-chloromethylpyridyl intermediate can begin with the starting compound and the chemistry disclosed in the PCT application PCT/US 91/03772 and the other PCT cases cited above. The chemistry set out in the '03772 case can be used to convert the starting material, 2,6-butidine-$\alpha^2$,3-diol, to, for example, the 2-(E-2-carboxymethylethenyl)3-[4-(4-methoxyphenyl)butyloxy]-6-chloromethylpyridine. This is illustrated in Scheme I given below. Novel chemistry, both conditions and the reagent DBU, are then used to couple the thiophenol with the chloromethyl substituted pyridine in order to make the basic structure of formula I. Base, or acid, can then be used to hydrolyze any ester group, if so desired. A free acid can be obtained from the salt by acidifying a solution of the salt. Esters and amides can be prepared using standard reaction conditions and reagents. Tetrazoles are prepared from the corresponding acid halide, e.g., the acid chloride, by literature methods.

Using the precursors prepared as per the noted PCT applications or which have been purchased from a commercial source, and the steps outlined in Scheme I, can be used to prepare compounds of formula I.

Scheme I

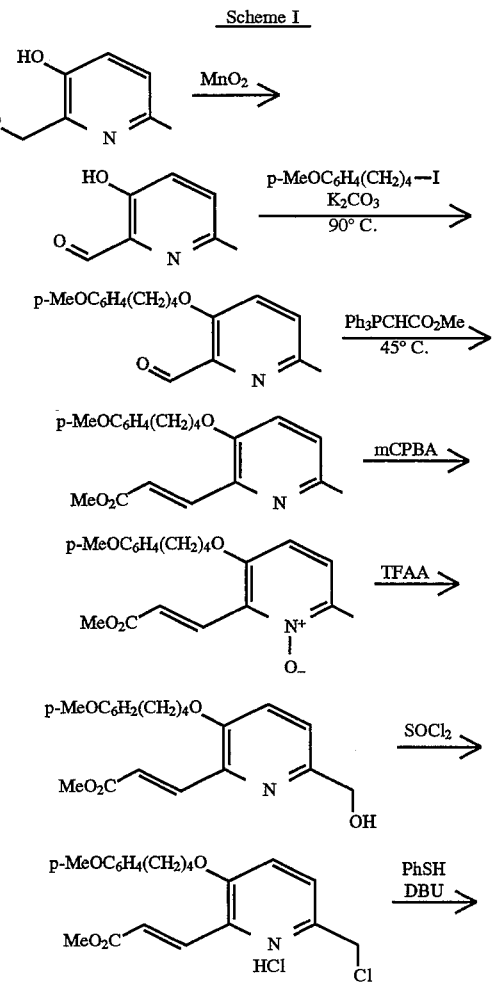

-continued
Scheme I

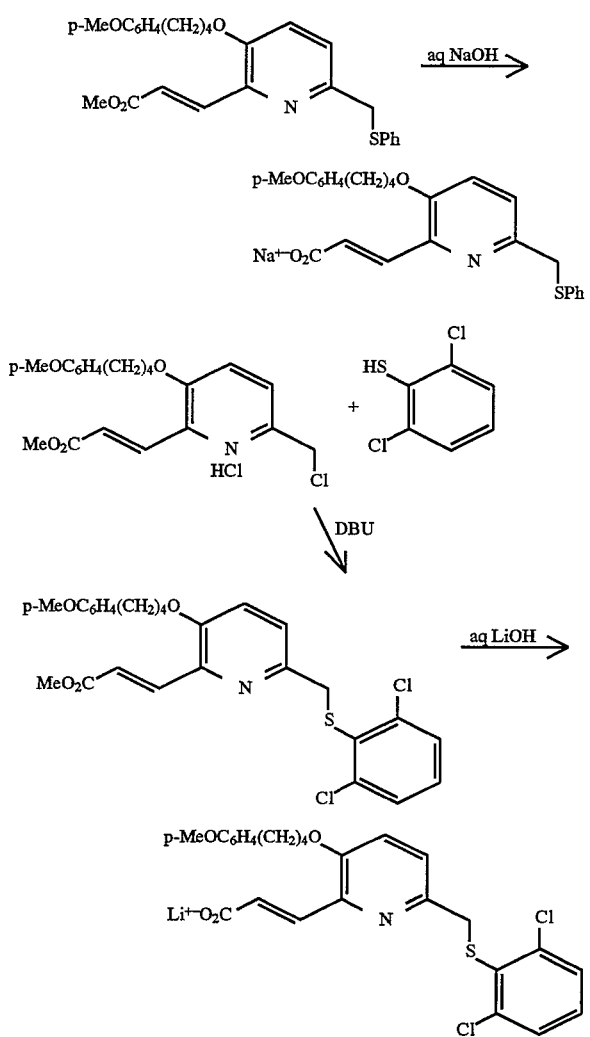

A general description of the conditions and reagents which can be used for converting the diol to the 6(chloromethyl)pyridine compound can be found in PCT application number PCT/US 91/03772. That description of the generalized case for each step is incorporated herein by reference along with the specific chemistry set out in the Examples of that application.

A number of thiophenols and thioalkylphenyl compounds useful for making the right hand portion of formula I can be purchased from commercial sources. A list, not intended to be exhaustive, is as follows: 2,5-dichlorothiophenol, 2,6-dimethylthiophenol, 2,4-dichlorothiophenol, 2-chloro-6-methylthiophenol, 2-chloro-4-fluorothiophenol, 2,4-dichlorobenzyl thiol, 2-chloro-6-fluorobenzyl mercaptan, and 2,4-difluorobenzyl thiol. Other thiols can be made by published chemistry; that chemistry involves converting a haloalkylphenyl (the bromo form is preferred) compound to the corresponding mercaptan by treating the bromo compound with thiourea followed by base hydrolysis. Alternatively the thiophenols can be prepared by thermal rearrangement of the corresponding thiocarbamate followed by hydrolysis.

Coupling the thiol with the chloromethylpyridyl compound using a novel method which employs 1,8-diazabicyclo[5.4.0]undec-7-ene (DBU) and an appropriate solvent, for example $CH_3CN$. Moisture is excluded from the system and an inert gas is used, for example argon. A slightly elevated temperature is preferred, one that is about 50° C. or so; the coupling reaction is complete in about 3 hours.

Once the core structure is prepared any ester can be hydrolyzed with acid or base, base is preferred, or that acid can be converted to another ester, an amide or another salt.

Pharmaceutical compositions of the present invention comprise a pharmaceutical carrier or diluent and some amount of a compound of the formula (I). The compound may be present in an amount to effect a physiological response, or it may be present in a lesser amount such that the user will need to take two or more units of the composition to effect the treatment intended. These compositions tony be made up as a solid, liquid or in a gaseous form. Or one of these three forms may be transformed to another at the rime of being administered such as when a solid is delivered by aerosol means, or when a liquid is delivered as a spray or aerosol.

Included within the scope of this disclosure is the method of treating a disease mediated by $LTB_4$ which comprises administering to a subject a therapeutically effective amount of a compound of formula I, preferably in the form of a pharmaceutical composition. For example, inhibiting the symptoms of an allergic response resulting from a mediator release by administration of an effective amount of a compound of formula I is included within the scope of this disclosure. The administration may be carried out in dosage units at suitable intervals or in single doses as needed. Usually this method will be practiced when relief of symptoms is specifically required. However, the method is also usefully carried out as continuous or prophylactic treatment. It is within the skill of the art to determine by murine experimentation the effective dosage to be administered from the dose range set forth above, taking into consideration such factors as the degree of severity of the condition or disease being treated, and so forth.

The nature of the composition and the pharmaceutical carrier or diluent will, of course, depend upon the intended route of administration, for example parenterally, topically, orally or by inhalation.

For topical administration the pharmaceutical composition will be in the form of a cream, ointment, liniment, lotion, pastes, aerosols, and drops suitable for administration to the skin, eye, ear, or nose.

For parenteral administration the pharmaceutical composition will be in the form of a sterile injectable liquid such as an ampule or an aqueous or non-aqueous liquid suspension.

For oral administration the pharmaceutical composition will be in the form of a tablet, capsule, powder, pellet, atroche, lozenge, syrup, liquid, or emulsion.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid parafins and mixtures thereof with water; for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The pharmaceutical preparations thus described are made following the conventional techniques of the pharmaceutical chemist as appropriate to the desired end product.

In these compositions, the amount of carrier or diluent will vary but preferably will be the major proportion of a suspension or solution of the active ingredient. When the diluent is a solid it may be present in lesser, equal or greater amounts than the solid active ingredient.

Usually a compound of formula I is administered to a subject in a composition comprising a nontoxic amount sufficient to produce an inhibition of the symptoms of a disease in which leukotrienes are a factor. Topical formulations will contain between about 0.01 to 5.0% by weight of the active ingredient and will be applied as required as a preventative or curative agent to the affected area. When employed as an oral, or other ingested or injected regimen, the dosage of the composition is selected from the range of from 50 mg to 1000 mg of active ingredient for each administration. For convenience, equal doses will be administered 1 to 5 times daily with the daily dosage regimen being selected from about 50 mg to about 5000 mg.

No unacceptable toxicological effects are expected when these compounds are administered in accordance with the present invention.

Bioassays

The specificity of the antagonist activity of a number of the compounds of this invention is demonstrated by relatively low levels of antagonism toward agonists such as potassium chloride, carbachol, histamine and $PGF_2$.

The receptor binding affinity of the compounds used in the method of this invention is measured by the ability of the compounds to bind to $[^3H]$-$LTB_4$ binding sites on human U937 cell membranes. The $LTB_4$ antagonist activity of the compounds used in the method of this invention is measured by their ability to antagonize in a dose dependent manner the $LTB_4$ elicited calcium transient measured with fura-2, the fluorescent calcium probe. The methods employed have been disclosed in prior published PCT application PCT/US 91/03772 which was filed 31 May 1991. The assays disclosed there are incorporated herein by reference.

SPECIFIC EMBODIMENTS

The following examples are given to illustrate how to make and use the compounds of this invention. These Examples are just that, examples, and are not intended to circumscribe or otherwise limit the scope of this invention. Reference is made to the claims for defining what is reserved to the inventors.

EXAMPLE 1

2-(E)-2-Carboxymethylethenyl)-3-[4-(4-methoxyphenyl)butyloxy]-6-chloromethylpyridine hydrochloride 1A 1-Iodo-4-(4-methoxyphenyl)butane.

To a stirred solution of 4-(4-methoxyphenyl)butan-1-ol (9.37 g, 52 mmol, Aldrich) in dry toluene (185 mL) under an argon atmosphere was added triphenylphosphine (17.8 g, 67.6 mmol) and imidazole (10.6 g, 156 mmol). After ten minutes $I_2$ (17.1 g, 67.6 mmol) was added. The reaction was then heated at 65° C. for 30 minutes. Upon cooling to room temperature the reaction was concentrated to ¼ volume. The remaining solution was diluted with $Et_2O$ and washed with $H_2O$ and brine and dried ($MgSO_4$). The solvent was removed and the resulting residue was dissolved in $CH_2Cl_2$ and applied to a flash chromatography column (silica). Elution with 2% EtOAc in hexane provided a colorless oil: $^1H$ NMR (250 MHz, $CDCl_3$) $\delta$7.08 (d, J=8.7 Hz, 2H, phenyl), 6.82 (d, J=8.7 Hz, 2H, phenyl), 3.78 (s, 3H, OMe), 3.17 (t, J=7.4 Hz, 2H, I-$CH_2$), 2.54 (t, J=7.2 Hz, 2H, benzylic), 1.85 (m, 2H, $CH_2$), 160 (m, 2H, $CH_2$).

1B 3-Hydroxy-6methyl-2-pyridine carboxaldehyde.

2,6-Lutidine-$\alpha^2$, 3-diol (15 g, 107.8 mmol, Aldrich) was suspended in dry $CH_2Cl_2$ (200 mL) an treated with $MnO_2$ (47 g, 539 mmol). The reaction was stirred at room temperature for 6 h. The reaction mixture was filtered through a pad of Celite and the solvent was evaporated. The crude aldehyde was obtained as a tan solid and was used directly for the next step: $^1H$ NMR (250 MHZ, $CDCl_3$) $\delta$10.65 (s, 1H, OH), 10.30 (s, 1H, aldehyde), 7.30 (m, 2H, 4,5-pyridyl), 2.55 (s, 3H, methyl).

1C 3-[4-(4-Methoxyphenyl)butyloxy]-6-methyl-2-pyridine carboxaldehyde.

To a solution of 1-iodo-4-(4-methoxyphenyl)butane (12.6 g, 43.4mmol) in dry DMF (45 mL,) under an argon atmosphere was added 3hydroxy-6-methyl-2-pyridine carboxaldehyde (7.2 g, 52.5 mmol) and anhydrous $K_2CO_3$ (30 g, 217 mmol). The reaction was vigorously stirred at 90° C. for 2.5 h. Upon cooling to room temperature the reaction was diluted with EtOAc and washed with $H_2O$, aq $NH_4Cl$, and brine and dried ($MgSO_4$). Evaporation provided crude aldehyde as a dark oil that was used without further purification.

1D 2-(E-2-Carboxymethylethenyl)-3-4-(4-methoxyphenyl)butyloxy]6-methylpyridine.

3-[4-(4-Methoxyphenyl)butyloxy]-6-methyl-2-pyridine carboxaldehyde obtained above was dissolved in dry toluene (100 mL) under an argon atmosphere and treated with methyl (triphenylphosphoranylidene)acetate (14.5 g, 43.4 mmol). The reaction was heated for 1 h at 50° C. Upon cooling to room temperature the reaction was diluted with EtOAc and washed with $H_2O$ and brine and dried ($MgSO_4$). Purification by flash column chromatography (silica, 20% EtOAc in hexane) gave a pale yellow oil: $^1H$ NMR (250 MHz, $CDCl_3$) $\delta$8.07 (d, J=15.7 Hz, 1H, vinyl), 7.10 (m, 4H, phenyl, 4,5-pyridyl), 7.07 (d, J=15.7 Hz, 1H, vinyl), 6.81 (d, J=8.7 Hz, 2H, phenyl), 3.97 (t, J=6.1 Hz, 2H, O-$CH_2$), 3.79 (s, 3H, OMe), 3.78 (s, 3H, methyl ester), 2.54 (t, J=7.2 Hz, 2H, benzylic), 2.48 (s, 3H, methyl), 1.85 (m, 2H, $CH_2$), 1.60 (m, 2H, $CH_2$); MS (ES): 356.4 (M+H).

1E 2-(E-2-Carboxymethylethenyl)-3-[4-(4-methoxyphenyl) butyloxy]-6-methylpyridine N-oxide.

2-(E-2-Carboxymethylethenyl)-3-[4-(4-methoxyphenyl) butyloxy]-6-methylpyridine (13.6 g, 38.2 mmol) was dissolved in dry $CH_2Cl_2$ (100 mL,) and cooled to 0° C. To this was added 50% mCPBA (13.2 g, 38.3 mmol) in three portions over 10 minutes. The cooling bath was removed and the reaction was stirred for 15 h at room temperature. The reaction was poured into aqueous $NaHCO_3$ and the product extracted into $CH_2Cl_2$. The organic extract was washed with $H_2O$ and brine and dried ($MgSO_4$). The crude product was obtained as a yellow solid and was used without further purification.

1F 2-(E-2-Carboxymethylphenyl)-3-[4-(4-methoxyphenyl) butyloxy]6-hydroxymethylpyridine.

2-(E-2-Carboxymethylethenyl)-3-[4-(4-methoxyphenyl) butyloxy]-6-methylpyridine N-oxide obtained above was suspended in dry DMF (100 mL) and cooled to 0° C. under an argon atmosphere. To this was slowly added trifluoroacetic anhydride (54 mL, 380 mmol). The reaction was maintained at 0° C. for 20 minutes followed by 18 h at room temperature. The reaction solution was slowly added to a solution of saturated aqueous $Na_2CO_3$ and stirred for 1h. The product was then extracted into EtOAc; the combined organic extracts were washed with $H_2O$ and brine and dried ($MgSO_4$). Purification by flash column chromatography (silica, EtOAc:hexane:$CH_2Cl_2$, 25:25:50) gave a waxy solid: $^1$H NMR (250 MHZ, $CDCl_3$) δ8.08 (d, J=15.7 Hz, 1H, vinyl), 7.23 (d, J=8.4 Hz, 1H, 5-pyridyl), 7.16 (d, J=8.4 Hz, 1H, 4-pyridyl), 7.09 (d, J=8.7 Hz, 2H, phenyl), 7.03 (d, J=15.7 Hz, 1H, vinyl), 6.82 (d, J=8.7 Hz, 2H, phenyl), 4.69 (d, J=4.1 Hz, 2H, $CH_2$-OH), 4.01 (t, J=6.1 Hz, 2H, O-$CH_2$), 3.82 s, 3H OMe), 3.78 (s, 3H, methyl ester), 3.62 (t, J=4.1 Hz, 1H, OH), 2.55 (t, J=7.2 Hz, 2H, benzylic), 1.85 (m, 2H, $CH_2$), 1.58 (m, 2H, $CH_2$); MS (CI): 374.3 (M+H).

1G 2-(E-2-Carboxymethylethenyl)-3-[4-(4-methoxyphenyl) butyloxy]-6-chloromethylpyridine hydrochloride 2-(E-2-Carboxymethylethenyl)-3-[4-(4-methoxyphenyl) butyloxy]-6-hydroxymethylpyridine (1.00 g, 2.69 mmol) was added to a cooled (0° C.) solution of $SOCl_2$ (1.96 mL, 26.9 mmol) in anhydrous toluene (20 mL) under an argon atmosphere. The cooling bath was removed and the reaction was stirred at room temperature for 4.5 h. The solvent and excess $SOCl_2$ were evaporated. The resulting crude product (tan solid) was used without further purification. This material served as the starting material for the preparation of the compounds set out in the following examples.

EXAMPLE 2

(E)-Lithium 3-[3-[4-(4-methoxyphenyl)butyloxy]-6-[(2.6-dichlorophenylthio)methyl]-2-pyridinyl]-2-propenoate 2A (E)-Methyl 3-[3-[4-(4-methoxyphenyl)butyloxy]-6-[(2,6-dichlorophenylthio)methyl]-2-pyridinyl]-2-propenoate.

2,6-Dichlorothiophenol (53 mg, 0.297 mmol, Aldrich) was dissolved in dry MeCN (0.60 mL,) and treated with 2-(E-2-carboxymethylethenyl)-3-[4-(4-methoxyphenyl) butyloxy]-6-chloromethylpyridine hydrochloride (115 mg, 0.270 mmol) and 1,8-diazabicyclo[5.4.0]undec-7-ene (DBU, 0.142 mL, 0.949 mmol). The reaction was stirred under an atmosphere of argon at 50° C. for 3 h. The reaction solution was diluted with EtOAc and washed with $H_2O$ and brine and dried ($MgSO_4$). Purification by flash column chromatography (silica, EtOAc: $CH_2Cl_2$: hexane, 10:15:75) gave a colorless waxy solid: $^1$H NMR (250 MHz, $CDCl_3$) δ7.94 (d, J=15.7 Hz, 1H, vinyl), 7.31 (d, J=7.6 Hz, 2H, aryl), 7.13 (m, 4H, aryl, pyridyl), 7.11 (d, J=8.4 Hz, 1H, pyridyl), 6.86 (d, J=8.7 Hz, 2H, phenyl), 6.69 (d, J=15.7 Hz, 1H, vinyl), 4.14 (s, 2H, $CH_2$-S), 3.97 (t, J=6.1 Hz, 2H, $CH_2$-O), 3.80 (s, 3H, OMe), 3.78 (s, 3H, methyl ester), 2.63 (t, J=7.2 Hz, 2H, benzylic), 1.81 (m, 4H, $CH_2CH_2$); analysis calcd. for $C_{27}H_{27}Cl_2NO_4S$: C, 60.90; H, 5.11; N, 2.63; found: C, 60.61; H, 5.01; N, 2.57; MS (ES+): 532.0 (M+H).

2B (E)-Lithium 3-[3-[4-(4-methoxyphenyl)butyloxy]-6-[(2.6-dichlorophenylthio)methyl]-2-pyridinyl]2-propenoate.

(E)-Methyl 3-[3-[4-(4-methoxyphenyl)butyloxy]-6-[(2,6-dichlorophenylthiomethyl]-2-pyridinyl]-2-propenoate (65 mg, 0.122 mmol) was dissolved in THF (1.0 mL) and MeOH (0.50 mL) and treated with 1.0M LiOH (0.25 mL, 0.25 mmol). The reaction was stirred under an argon atmosphere for 20 h. The solvent was evaporated and the product purified by Reversed Phased MPLC (RP-18 silica, $H_2O$-MeOH gradient). Lyophilization yielded a colorless amorphous solid: $^1$H NMR (250 MHz, $d^4$-MeOH) δ7.68 (d, J=15.7 Hz, 1H, vinyl), 7.37 (d, J:=7.6 Hz, 2H, aryl), 7.13 (m, 4H, aryl, pyridyl), 7.02 (d, J=8.4 Hz, 1H, pyridyl), 6.82 (d, J=15.7 Hz, 1H, vinyl), 6.81 (d, J=8.7 Hz, 2H, phenyl), 4.13 (s, 2H, CH-S), 4.00 (t, J=6.1 Hz, 2H, $CH_2$O), 3.75 (s, 3H, OMe), 2.62 (t, J=7.2 Hz, 2H, benzylic), 1.80 (m, 4H, $CH_2CH_2$); analysis calcd. for $C_{26}H_{24}Cl_2NO_4SLi \cdot ^{15}{}_8H_2O$; C, 55.95; H, 5.01; N, 2.51; found: C, 55.75; H, 4.58; N, 2.36; MS (ES+): 518.0 (M+H, free acid).

Proceeding in a similar manner, but substituting for the 2,6-dichlorophenol the appropriate thiophenol or mercaptan, the following compounds were made:

(E)-sodium 3-[3-[4-(4-methoxyphenyl)butyloxy]-6-[(2,6-difluorophenylthio)methyl]-2-pyridinyl]-2-propenoate, (E)-sodium 3-[3-[4-(4-methoxyphenyl)butyloxy]-6-[(2,6-dimethylphenylthio)methyl]-2-pyridinyl]-2-propenoate, (E)-sodium 3-[3-[4-(4-methoxyphenyl)butyloxy]-6-[(2,6-dichlorobenzylthio)methyl]-2-pyridinyl]-2-propenoate, (E)-sodium 3-[3-[4-(4-fluorophenyl)butyloxy]-6[(2,6-dichlorophenylthio)methyl]-2-pyridinyl]-2-propenoate, (E)-sodium 3-[3-[4-(4-fluorophenyl)butyloxy]-6[(2,6-difluorophenylthio)methyl]-2-pyridinyl]-2-propenoate, (E)-sodium 3-[3-[2-(4-fluorophenyl)ethyloxy]-6[(2,6-dichlorophenylthio)methyl]-2-pyridinyl]-2-propenoate, (E)-sodium 3-[3-[2-(4-fluorophenyl)ethyloxy]-6[(2,6-difluorophenylthio)methyl]-2-pyridinyl]-2-propenoate, (E)-sodium 3-[3-(4-fluorobenzyloxy)-6[(2,6-dichlorophenylthio)methyl]-2-pyridinyl]-2-propenoate, (E)-sodium 3-[3-[4-phenylbutyloxy]-6[(2,6-dichlorophenylthio)methyl]-2-pyridinyl]-2-propenoate, (E)-sodium 3-[3-[4-phenylethyloxy]-6[(2,6-dichlorophenylthio)methyl]-2-pyridinyl]-2-propenoate, sodium 3-[3-[2-(4-fluorophenyl)ethyloxy]-6-[(2,6-dichlorophenylthio)methyl]-2-pyridinyl]-2-propanoate, sodium 3-[3-[4-(4-fluorophenyl)butyloxy]-6-[(2,6-dichlorophenylthio)methyl]-2-pyridinyl]-2-propanoate, sodium 3-[3-[4-(4-methoxyphenyl)butyloxy]-6-[(2,6-dichlorophenylthio)methyl]-2 -pyridinyl]-2-propanoate, (E)-sodium 3-[3-[2-(4-methoxyphenyl)ethyloxy]-6-[(2,6-dichlorophenylthio)methyl]-2-pyridinyl]-2-propenoate, (E)-sodium 3-[3-[2-(4-fluorophenyl)ethyloxy]-6-[(2-chloro-6-methylphenylthio)methyl]-2-pyridinyl]-2-propenoate, sodium 3-[3-[2-(4-methoxyphenyl)ethyloxy]-6-[(2,6-dichlorophenylthio)methyl]-2-pyridinyl]-2-propanote, and (E)-sodium 3-[3-[4-(4-methoxyphenyl)butyloxy]-6-[(2,6-dimethoxyphenylthio)methyl]-2-pyridinyl]-2-propenoate.

EXAMPLE 3

Preparation of Free Acids

The acid form of any of the foregoing salts were prepared by dissolving the salt in water if it is not already in solution, then acidifying that solution with an acid such as a mineral acid eg. dilute (6N) HCl. The acid was recovered by filtering out the precipitate. In that manner, and using the process disclosed in Examples 1–3, the following compounds were prepared:

(E)-3-[3-[2-(4-chlorophenyl)ethyloxy]-6[(2,6-dichlorophenylthio)methyl]-2-pyridinyl]-2-propenoic acid, (E)-3-[3-[(4-methoxyphenyl)octyloxy]- 6[(2,6-dichlorophenylthio)methyl]-2-pyridinyl]-2-propenoic acid, (E)-3-[3-[2-phenethyloxy]-6-[(2,6-dichlorophenylthio)methyl]-2-pyridinyl]-2-propenoic acid, (E)-3-[3-[3-phenylpropyloxy]-6-[(2,6-dichlorophenylthio)methyl]-2-pyridinyl]-2-propenoic acid, (E)-3-[3-[2-phenethyloxy]-6-[(2,6-dichlorophenyloxy)methyl]-2-pyridinyl]-2-propenoic acid, (E)-3-[3-[2-(thien-2-yl)ethyloxy]-6-[(2,6-dichlorophenylthio)methyl]-2-pyridinyl]-2-propenoic acid, (E)-3-[3-[2-(thien-3-yl)ethyloxy]-6[(2,6-dichlorophenylthio)methyl]-2-pyridinyl]-2-propenoic acid, and (E)-3-[3-[2-(3-methylthiazol-2-yl)ethyloxy]-6[(2,6-dichlorophenylthio)methyl]-2-pyridinyl]-2-propenoic acid.

EXAMPLE 4

(E)-N,N,-Diethyl 3-[3-[2-phenethyloxy]-6-[(2,6dichlorophenylthio)methyl]-2-pyridinyl]-2-propenamide 4A 2-(E-2-Carboxymethylethenyl)-3-(2-phenethyloxy)-6-hydroxymethylpyridine.

This was prepared by an analogous procedure to that described for the preparation of 1F, substituting phenethyl bromide for 1-iodo-4-(4-methoxyphenyl)butane.

4B 2-(E-2-Carboxyethenyl)-3-(2-phenethyloxy)-6-hydroxymethylpyridine.

To a stirred solution of 2-(E-2-carboxymethylethenyl)-3-(2-phenethyloxy)-6-hydroxymethylpyridine (150 mg, 0.49 mmol) in 1:2 MeOH-THF (3 mL) was added 1M NaOH (0.98 mL, 0.98 mmol). The reaction was stirred at room temperature for 24 h, then adjusted to pH 4.5 using 5% HCl. The solvents were evaporated and the crude carboxylic acid was dried under reduced pressure to give the noted compound: $^1$H NMR (250 MHz, CDCl$_3$) δ8.11 (d, J=15.7 Hz, 1H, vinyl), 7.33–7.19 (m, 7H, aryl), 6.99 (d, J=15.7 Hz, 1H, vinyl), 4.68 (s, 2H, CH$_2$-O), 4.19 (t, J=6.1 Hz, 2H, O-CH$_2$), 3.13 (t, J=7.2 Hz, 2H, benzylic).

4C (E)- N,N,-Diethyl 3-[3-[2-phenethyloxy]-6-[hydroxymethyl]-2-pyridinyl]-2-propenamide.

To a solution of 2-(E-2-carboxyethenyl)-3-(2phenethyloxy)-6-hydroxymethylpyridine (143.3 mg, 0.48 mmol) in DMF (1 mL) under an argon atmosphere was added t-butylchlorodimethylsilane (172.8 mg, 1.15 mmol) and imidazole (163.2 mg, 2.40 mmol). The reaction was stirred at room temperature for 18 h and then partitioned between EtOAc and H$_2$O. The organic phase was washed with aqueous NaHCO$_3$ and dried (MgSO$_4$).

To a cooled (0° C.) solution of the disilylated intermediate, prepared above, in CH$_2$Cl$_2$(1 mL) was added oxalyl chloride (75 mg, 0.60 mmol) and catalytic DMF (1 drop). The reaction was stirred at 0° C. for 1.5 h, then at room temperature for 0.5 h. The solvent was evaporated and the acid chloride was suspended in THF (1 mL). To this solution was added diethylamine (0.5 mL, 4.8 mmol THF (1 mL). The reaction solution was stirred at room temperature for 45 minutes, then partitioned between EtOAc and H$_2$O. The organic phase was washed with H$_2$O and dried (MgSO$_4$).

To a cooled (0° C.) solution of the silylether in THF (1 mL) was added tetrabutylammonium fluoride (1.44 mL, 1.4 mmol, 1M in THF). The cooling bath was removed and the reaction was stirred at room temperature for 1.5 h. The reaction was quenched with H$_2$O and the product was extracted into EtOAc. The organic phase was washed with H$_2$O and dried (MgSO4). Purification by flash column chromatography (silica, 3% MeOH in CH$_2$Cl$_2$) gave an oil: $^1$ H NMR (250 MHz, CDCl$_3$) δ8.09 (d, J=15.7 Hz, 1H, vinyl), 7.71 (d, J=15.7 Hz, 1H, vinyl), 7.32 (m, 5H, aryl), 7.26 (s, 2H, aryl), 4.75 (s, 2H, CH$_2$-O), 4.24 (t, J=6.1 Hz, 2H, OCH$_2$), 3.55 (m, 4H, amide CH$_2$), 3.19 (t, J=7.2 Hz, 2H, benzylic), 1.28 and 1.23 (triplets, J=7.0 Hz, 6H, amide Me).

4D (E)-N,N-Diethyl 3-[3-2-phenethyloxy]-6-[(2.6-dichlorophenylthio)methyl]-2-pyridinyl]-2 -propenamide.

To a cooled (0° C.) solution of the primary alcohol (35 mg, 0.10 mmol) in toluene (0.5 mL) was added thionyl chloride (119 mg, 1.0 mmol). The reaction was stirred at room temperature for 1.5h. The solvent and excess reagent were evaporated giving the crude chloromethyl hydrochloride compound.

The remainder of the synthesis was completed using an identical procedure to that described for 2A by coupling with 2,6-dichlorothiophenol to give the product as an oil: $^1$H NMR (400 MHz, CDCl$_3$) δ7.98 (d, J=15.7 Hz, 1H, vinyl), 7.30 (m, 8H, aryl, vinyl), 7.10 (m, 2H, aryl), 6.99 (d, 1H, aryl), 4.17 (s, 2H, CH$_2$-S), 4.12 (t, J=6.1 Hz, 2H, OCH$_2$), 3.50 (m, 4H, amide CH$_2$), 3.11 (t, J=7.2 Hz, 2H, benzylic), 1.25 and 1.18 (triplets, J=7.0 Hz, 6H, amide Me); Analysis calcd. for C$_{27}$H$_{28}$Cl$_2$N$_2$O$_2$S.¼H$_2$O: C, 62.37; H, 5.52; N, 5.39; found: C, 62.07; H, 5.13; N, 5.39; MS (ES): 515.0 (M+H).

EXAMPLE 5

Formulations for pharmaceutical use incorporating compounds of the present invention can be prepared in various forms and with numerous excipients. Means for making various formulations can be found in standard texts such as Remington's Pharmaceutical Sciences, and similar publications and compendia. Specific examples of formulations are given below.

OINTMENTS

Hydrophyllic Petrolatum

| Ingredients | Amount (% Weight/weight) |
|---|---|
| Cholesterol | 30.0 g |
| Stearyl Alcohol | 30.0 g |
| White Wax | 78.0 g |
| Active Ingredient | 2.0 g |
| White Petrolatum | 860.0 g |

The stearyl alcohol, white wax and white petrolatum are melted together (steam bath for example) and cholesterol and the active ingredient are added. Stirring is commenced and continued until the solids disappear. The source of heat is removed and the mix allowed to congeal and packaged in metal or plastic tubes.

| Ingredients | Amount (% W/W) |
|---|---|
| Methylparaben | 0.25 g |
| Propylparaben | 0.15 |

-continued

| Ingredients | Amount (% W/W) |
|---|---|
| Sodium Laurly Sulfate | 10.0 g |
| Active Ingredient | 5.0 g |
| Propylene Glycol | 120.0 g |
| Stearyl Alcohol | 250.0 g |
| White Petrolatum | 250.0 g |
| Purified Water | QS to 1000.0 g |

The stearyl alcohol and white petrolatum are combined over heat. Other ingredients are dissolved in water, then this solution is added to the warm (ca 50° to 100° C. alcohol/petrolatum mixture and stirred until the mixture congeals. It can then be packed in tubes or another appropriate package form.

EXAMPLE 6

Inhalation Formulation

A compound of formula I, 1 to 10 mg, is dissolved in isotonic saline and aerosolized from a nebulizer operating at an air flow adjusted to deliver the desired amount of drug per use.

What is claimed is:
1. A compound of formula I

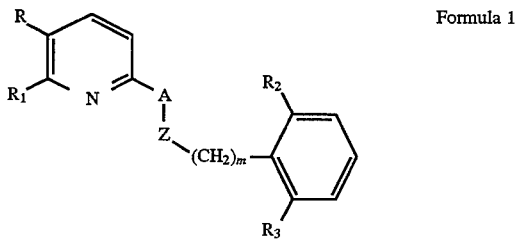

Formula 1 or an N-oxide, or a pharmaceutically acceptable salt, where

A is $CH_2$ and Z is $S(O)_q$ where q is 0, 1 or 2, $CH_2$, CHOH, CO, $NR_x$, or O, or A is C=O and Z is $NR_x$;

m is 0–5;

$R_x$ is hydrogen or lower alkyl;

R is $C_1$ to $C_{20}$-aliphatic, unsubstituted or substituted five-membered heteroaryl-$C_1$ to $C_{10}$-aliphatic-O—, unsubstituted or substituted phenyl-$C_1$ to $C_{10}$-aliphatic where substituted phenyl has one or more radicals selected from the group consisting of lower alkoxy, lower alkyl, trihalomethyl, and halo, or R is $C_1$ to $C_{20}$-aliphatic-O—, or R is unsubstituted or substituted phenyl-$C_1$ to $C_{10}$-aliphatic-O—where substituted phenyl has one or more radicals selected from the group consisting of lower alkoxy, lower alkyl, trihalomethyl, and halo;

$R_1$ is $R_4$, —($C_1$ to $C_5$ aliphatic)$R_4$, —($C_1$ to $C_5$ aliphatic) CHO, —($C_1$ to $C_5$ aliphatic)$CH_2OR_5$;

$R_2$ and $R_3$ are independently, halo, lower alkoxy, $CF_3$, CN, or lower alkyl;

$R_4$ is tetrazol-5-yl or COOH or an ester or amide thereof; and $R_5$ is H, lower alkyl, $CH_3(CH_2)_{0-6}CO$ or phenyl$(CH_2)_{0-3}CO$.

2. A compound of claim 1 where R is $C_8$ to $C_{20}$ alkoxy, thienyl $C_1$ to $C_{10}$ alkoxy, substituted thiazolyl-$C_1$ to $C_{10}$ alkoxy, phenyl-$C_1$ to $C_{10}$ alkoxy or substituted-phenyl$C_1$ to $C_{10}$ alkoxy; $R_1$ is —($C_1$–$C_3$-alkyl)$R_4$, or —($C_2$–$C_3$alkenyl)$R_4$.

3. A compound of claim 2 where R is thien-2-ylethyloxy, thien-3-ylethyloxy, 3-methylthiazol-2-ylethyloxy, substituted phenyl-$C_4$ to $C_{10}$ alkoxy, or $CH_3(CH_2)_{7-9}$-O—; m is 0,1 or 2; $R_1$ is $HO_2C$—CH=CH— or $HO_2C$—$CH_2CH_2$— or a salt, ester or amide thereof.

4. A compound of claim 3 where $R_2$ and $R_3$ are both halo or both methyl.

5. A compound of claim 4 which is (E)-lithium 3-[3-[4-(4-methoxyphenyl)butyloxy]-6-[(2,6-dichlorophenylthio) methyl]-2-pyridinyl]-2-propenoate, (E)-sodium 3-[3-[4-(4-methoxyphenyl)butyloxy]-6-[(2,6-difluorophenylthio)methyl]-2-pyridinyl]-2-propenoate, (E)-sodium 3-[3-[4-(4-methoxyphenyl)butyloxy]-6-[(2,6-dimethylphenylthio)methyl]-2-pyridinyl]-2-propenoate, (E)-sodium 3-[3-[4-(4-methoxyphenyl)butyloxy]-6-[(2,6-dimethoxyphenylthio)methyl]-2-pyridinyl]-2-propenoate, (E)-sodium 3-[3-[4-(4-fluorophenyl)butyloxy]-6-[(2,6-dichlorophenylthio)methyl]-2-pyridinyl]-2-propenoate, (E)-sodium 3-[3-[4-(4-fluorophenyl)butyloxy]-6-[(2,6-difluorophenylthio)methyl]-2-pyridinyl]-2-propenoate, (E)-sodium 3-[3-[2-(4-fluorophenyl)ethyloxy]-6-[(2,6-dichlorophenylthio)methyl]-2-pyridinyl]-2-propenoate, (E)-sodium 3-[3-[2-(4-fluorophenyl)ethyloxy]-6-[(2,6-difluorophenylthio)methyl]-2-pyridinyl]-2-propenoate, (E)-sodium 3-[3-(4-fluorobenzyloxy)-6-[(2,6-dichlorophenylthio)methyl]-2-pyridinyl]-2propenoate, (E)-sodium 3-[3-[4-phenylbutyloxy]-6-[(2,6-dichlorophenylthio)methyl]-2-pyridinyl]-2-propenoate, (E)-sodium 3-[3-[4-phenylethyloxy]-6-[(2,6-dichlorophenylthio)methyl]-2-pyridinyl]-2-propenoate, sodium 3-[3-[2-(4-fluorophenyl)ethyloxy]-6-[(2,6-dichlorophenylthio)methyl]-2-pyridinyl]-2-propanoate, sodium 3-[3-[4-(4-fluorophenyl)butyloxy]-6-[(2,6-dichlorophenylthio)methyl]-2-pyridinyl]-2-propanoate, sodium 3-[3-[4-(4-methoxyphenyl)butyloxy]-6-[(2,6-dichlorophenylthio)methyl]-2-pyridinyl]-2-propanoate, (E)-sodium 3-[3-[2-(4-methoxyphenyl) ethyloxy]-6-[(2,6-dichlorophenylthio)methyl]-2-pyridinyl]-2-propenoate, (E)-sodium 3-[3-[2-(4-fluorophenyl)ethyloxy]-6-[(2-chloro-6-methylphenylthio)methyl]-2-pyridinyl]-2-propenoate, sodium 3-[3-[2-(4-methoxyphenyl)ethyloxy]-6-[(2,6-dichlorophenylthio)-methyl]-2-pyridinyl]-2-propanoate, (E)-3-[3-[2-(4-chlorophenyl)ethyloxy]-6-[(2,6-dichlorophenylthio)methyl]-2-pyridinyl]-2-propenoic acid, (E)-3-[3-[8 -(4-methoxyphenyl)octyloxy]-6-[(2,6-dichlorophenylthio)methyl]-2-pyridinyl]-2-propenoic acid, (E)-3-[3-[2-phenethyloxy]-6-[(2,6-dichlorophenylthio) methyl]-2-pyridinyl]-2-propenoic acid, (E)-3-[3-[3-phenylpropyloxy]-6-[(2,6-dichlorophenylthio)methyl]-2-pyridinyl]-2-propenoic acid, (E)-N,N-diethyl 3-[3-[2-phenethyloxy]-6-[(2,6-dichlorophenylthio)methyl]-2-pyridinyl]-2-propenamide, (E)-3-[3-[2-phenethyloxy]-6-[(2,6-dichlorophenyloxy) methyl]-2-pyridinyl]-2-propenoic acid, (E)-3-[3-[2-(thien-2-yl) ethyloxy]-6-[(2,6-dichlorophenylthio)methyl]-2-pyridinyl]-2-propenoic acid, ( (E)-3-[3-[2-(thien-3-yl)ethyloxy]-6-[(2,6-dichlorophenylthio)methyl]-2-pyridinyl]-2-propenoic acid, (E)-3-[3-[2-(3-methylthiazol-2-yl)ethyloxy]-6-[(2,6-dichlorophenylthio)methyl]-2-pyridinyl]-2-propenoic acid, or a free acid thereof or another pharmaceutically acceptable salt.

6. A method for treating psoriasis which comprises administering an effective mount of a compound of formula I according to claim 1 alone or admixed with a suitable carrier.

7. A composition comprising a pharmaceutically acceptable carrier and a compound according to claim 1.

8. A method for treating inflammatory bowel disease which comprises administering an effective amount of a compound of formula I according to claim 1 alone or admixed with a suitable carrier.

9. A compound according to claim 1 wherein A is $CH_2$ and Z is $S(O)_q$ or O.

10. A compound according to claim 1 wherein $R_1$ is —($C_1$ to $C_3$alkyl)$R_4$ or —($C_2$ to $C_3$alkenyl) $R_4$ and $R_2$ and $R_3$ are halo.

11. A compound according to claim 1 wherein $R_1$ is —$CH_2CH_2CO_2H$ or —$CH=CHCO_2H$.

12. A compound according to claim 1 wherein $R_2$ and $R_3$ are chloro.

13. A compound according to claim 1 wherein R is unsubstituted phenyl$(CH_2)_{2-8}$-O—, or the p-fluoro- or p-methoxyphenyl$(CH_2)_{2-8}$-O— group.

14. A compound according to claim 1 which is: (E)-3-[3-[2-phenethyloxy]-6-[(2,6-dichlorophenylthio)methyl]-2-pyridinyl]-2-propenoic acid, or a pharmaceutically acceptable salt thereof.

* * * * *